United States Patent [19]

Clitherow

[11] Patent Number: 4,482,552

[45] Date of Patent: Nov. 13, 1984

[54] TRIAZOLE COMPOUNDS AND THEIR PHARMACEUTICAL USE

[75] Inventor: John W. Clitherow, Hertfordshire, England

[73] Assignee: Glaxo Group Limited, London, England

[21] Appl. No.: 469,233

[22] Filed: Feb. 24, 1983

[30] Foreign Application Priority Data

Feb. 26, 1982 [GB] United Kingdom ................ 8205723

[51] Int. Cl.$^3$ .................... A61K 31/41; C07D 403/12; C07D 403/14

[52] U.S. Cl. ............................... 424/246; 424/248.51; 424/248.54; 424/248.56; 424/263; 424/267; 424/269; 424/270; 544/60; 544/124; 544/132; 546/193; 546/194; 546/210; 548/161; 548/212; 548/266

[58] Field of Search ........................ 544/60, 124, 132; 546/163, 194, 210; 548/266, 161, 212; 424/246, 248.51, 248.54, 248.56, 263, 267, 269, 270

[56] References Cited

U.S. PATENT DOCUMENTS 4,318,913 3/1982 Clitherow et al. .................. 546/210
4,323,566 4/1982 Clitherow et al. ............. 424/248.51

Primary Examiner—Robert T. Bond
Attorney, Agent, or Firm—Bacon & Thomas

[57] ABSTRACT

Compounds of the general formula (I)

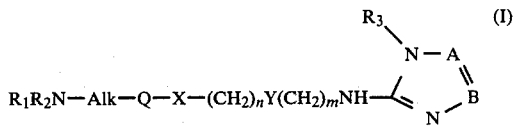

and physiologically acceptable salts, hydrates and bio-precursors thereof have been found to show pharmacological activity as selective histamine $H_2$-antagonists.

The substituents in Formula (I) are defined in the specification.

10 Claims, No Drawings

TRIAZOLE COMPOUNDS AND THEIR PHARMACEUTICAL USE

This invention relates to heterocyclic derivatives having action on histamine receptors, to processes for the preparation of the said heterocyclic derivatives, to pharmaceutical compositions containing the said derivatives and to the use of these derivatives in therapeutics.

Certain heterocyclic derivatives have now been found to possess potent activity as $H_2$-antagonists. These compounds, which are more particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in British Patent Specification No. 1565966 modified by the use of sodium pentobarbitone (50 mg/kg) as anaesthetic instead of urethane, and in conscious dogs equipped with Heidenhain pouches using the methods described by Black et al, Nature 1972 236, 385. Furthermore the compounds antagonise the effect of histamine on the contraction frequency of isolated guinea pig right atrium.

Compounds with histamine $H_2$-blocking activity may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator. Thus they may be used for example, either alone or in combination with other active ingredients in the treatment of allergic and inflammatory conditions of the skin.

The present invention provides compounds of the general formula (I)

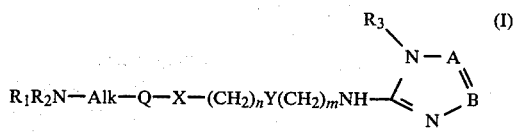

and physiologically acceptable salts, and hydrates thereof, in which $R_1$ represents hydrogen, $C_{1-14}$ alkyl, cycloalkyl, alkenyl, aralkyl, heteroaralkyl, trifluoroalkyl, or alkyl substituted by hydroxy, alkoxy, amino, alkylamino, dialkylamino or cycloalkyl; and $R_2$ represents hydrogen or $C_{1-4}$ alkyl; or $R_1$ and $R_2$ may together with the nitrogen atom to which they are attached form a 5 to 10 membered ring which may be saturated or may contain at least one double bond, may be unsubstituted or may be substituted by one or more $C_{1-3}$ alkyl e.g. methyl, groups or a hydroxy group and/or may contain another heteroatom selected from oxygen and sulphur;

Alk represents a straight or branched alkylene chain of 1 to 3 carbon atoms,

Q represents a furan or thiophene ring in which incorporation into the rest of the molecule is through bonds at the 2- and 5-positions, the furan or thiophene ring optionally bearing a further substituent $R_4$ adjacent to the group $R_1R_2N$—Alk—; or Q represents a thiophene ring in which incorporation into the rest of the molecule is through bonds at the 2- and 4-positions, the thiophene ring optionally bearing a further substituent $R_4$ adjacent to the group $R_1R_2NAlk$ with the proviso that when the group $R_1R_2NAlk$ is in the 4-position then the group $R_4$ is in the 5-position; or Q represents a benzene ring in which incorporation into the rest of the molecule is through bonds at the 1- and 3- or 1- and 4-positions;

$R_4$ represents halogen or $C_{1-4}$ alkyl which may be substituted by hydroxy or $C_{1-4}$ alkoxy;

X represents oxygen, sulphur, —NH—, methylene or a bond;

Y represents oxygen, sulphur, methylene or a bond;

n represents zero, 1, 2 or 3, and m is an integer from 2 to 5, with the provisos that (a) the total number of atoms in the chain $X(CH_2)_nY(CH_2)_m$ is an integer from 3 to 8, (b) when X and Y represent oxygen or sulphur then n is 2 or 3, (c) when X represents —NH— then Q is a benzene ring and Y represents methylene or a bond, and (d) when Q represents a benzene ring, X represents oxygen, and n represents 1, then m may additionally represent 1 and Y may additionally represent —$CHR_6$ where $R_6$ represents hydrogen or acyl; and $R_3$ represents hydrogen, alkyl, alkenyl, aralkyl, or $C_{2-6}$ alkyl substituted by hydroxy or alkoxy;

either A represents N and B represents $CR_5$; or A represents $CR_5$ and B represents N; and $R_5$ represents an aralkyl or heteroaralkyl group in which the alkyl portion is substituted by hydroxy, alkoxy or acyloxy.

In the above formula (I) the term "alkyl" as a group or part of a group means that the group is straight or branched and, unless otherwise stated, contains 1 to 6 carbon atoms, and in particular 1 to 4 carbon atoms, e.g. methyl or ethyl, and the term "alkenyl" means that the group has preferably 3 to 6 carbon atoms. The term "cycloalkyl" means that the group has 3 to 8 carbon atoms. The term "aryl" as a group or part of a group preferably means phenyl or substituted phenyl, for example phenyl substituted with one or more $C_{1-3}$ alkyl or $C_{1-3}$ alkoxy groups, or halogen atoms, e.g. fluorine. The term "acyl" means an aroyl, aralkanoyl or $C_{1-6}$ alkanoyl group, e.g. acetyl, formyl, phenylacetyl or benzoyl. The term "heteroaryl" as a part of a group within the definition of $R_1$ means a 5 or 6 membered monocyclic ring containing 1 to 3 heteroatoms selected from oxygen, nitrogen and sulphur, e.g. thienyl, pyridyl, furyl or thiazolyl. The heteroaryl ring may be unsubstituted or substituted by $C_{1-3}$ alkyl, $C_{1-3}$ alkoxy, hydroxy, hydroxyalkyl, aminoalkyl, alkylaminoalkyl, dialkylaminoalkyl or halogen. The term "heteroaryl" as part of a group within the definition of $R_5$ means a 5 or 6 membered monocyclic ring containing one heteroatom selected from oxygen, nitrogen and sulphur, e.g. thienyl, pyridinyl or furyl, optionally substituted by a $C_{1-3}$ alkyl group. The alkyl portion of a heteroaralkyl group is a straight or branched $C_{1-4}$ alkyl chain, and the heteroaryl ring is linked to the alkyl portion through a carbon atom.

One aspect of the invention relates to compounds of formula (I) in which $R_1$, $R_2$, $R_3$, Alk, Q, X, Y, n and m are as defined above but excluding the additional possibilities for m and Y given by proviso (d).

Preferred compounds of formula (I) are those in which $R_1$ represents $C_{1-8}$ alkyl (e.g. methyl, propyl, butyl or heptyl), $C_{1-4}$ alkyl substituted by a trifluoromethyl group (e.g. 2,2,2-trifluoroethyl), $C_{2-4}$ alkyl substituted by hydroxy or a di $C_{1-3}$ alkyl amino group (e.g. 3-hydroxypropyl or dimethylaminoethyl), $C_{5-7}$ cycloalkyl (e.g. cyclohexyl), $C_{3-5}$ alkenyl (e.g. allyl), phenyl $C_{1-3}$ alkyl (e.g. benzyl), or a heteroaryl $C_{1-3}$ alkyl group where the heteroaryl ring contains one heteroatom (e.g. 2-furylmethyl);

$R_2$ represents hydrogen or methyl; or $R_1R_2N$ represents a 5-8 membered ring optionally containing a double bond, an oxygen atom or an alkyl (e.g. methyl) substituent (e.g. piperidino, morpholino, 4-methylpiperidino, pyrrolidino, hexamethylenimino or tetrahydropyridino);

Alk represents methylene;

Q represents a benzene ring incorporated into the rest of the molecule through bonds at the 1- and 3- positions; or a furan ring incorporated into the rest of the molecule through bonds at the 2- and 5- positions optionally bearing a substituent $R_4$ adjacent to the group $R_1R_2NAlk$ where $R_4$ is $C_{1-4}$ alkyl (e.g. methyl); or a thiophene ring incorporated into the rest of the molecule through bonds at the 2- and 4-positions with the substituent $R_1R_2NAlk$ in the 2-position; with the provisos that when Q is a benzene ring as just defined, then X is a bond, n is zero, Y is oxygen and m is 3, 4 or 5, or X and Y both represent oxygen and n and m are both 2, or X is oxygen, Y is CHOH and n and m are both 1; and when Q is a furan or thiophene ring as just defined, then X is a bond and either Y is sulphur or $CH_2$, n is 1 and m is 2, or Y is oxygen, n is 1 and m is 3;

$R_3$ represents hydrogen or alkyl (e.g. methyl);

$R_5$ represents phenyl $C_{1-3}$ alkyl (e.g. benzyl) or heteroaryl $C_{1-3}$ alkyl (e.g. furylmethyl or pyridylmethyl) in which the alkyl portion is substituted by hydroxy, $C_{1-4}$ alkanoyloxy (e.g. acetyloxy) or $C_{1-2}$ alkoxy (e.g. methoxy).

Within the preferred meaning of $R_5$ compounds in which $R_5$ is defind as follows can be regarded as a separate aspect of the invention, $R_5$ represents phenyl $C_{1-3}$ alkyl (e.g. benzyl) in which the alkyl portion is substituted by $C_{1-4}$ alkanoyloxy (e.g. acetyloxy) or $C_{1-2}$ alkoxy (e.g. methoxy), or heteroaryl $C_{1-3}$ alkyl (e.g. furylmethyl or pyridylmethyl) in which the alkyl portion is substituted by hydroxy, $C_{1-4}$ alkanoyloxy (e.g. acetyloxy) or $C_{1-2}$ alkoxy (e.g. methoxy).

A particularly preferred group of compounds are those of formula (II)

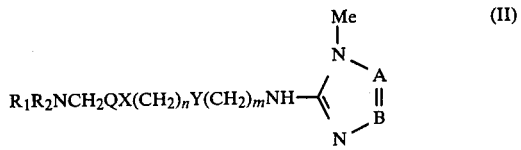

in which $R_1R_2N$ represents $diC_{1-3}$ alkylamino (e.g. dimethylamino), furylmethylamino, or pyrrolidino, piperidino, 4-methylpiperidino, tetrahydropyridino or hexamethylenimino, more preferably piperidino;

A represents N and B represents $CR_5$, or A represents $CR_5$ and B represents N, where $R_5$ represents phenyl $C_{1-3}$ alkyl (e.g. benzyl) or heteroaryl $C_{1-3}$ alkyl (e.g. furylmethyl or pyridylmethyl) in which the alkyl portion is substituted by hydroxy, or phenyl $C_{1-3}$ alkyl (e.g. benzyl) in which the alkyl portion is substituted by $C_{1-4}$ alkanoyloxy (e.g. acetyloxy) or $C_{1-2}$ alkoxy (e.g. methoxy);

either Q is 1,3-benzene, and X is a bond, n is zero, Y is oxygen and m is 3 or 4, more preferably 3; or X is oxygen, n is 1, Y is —CHOH— and m is 1; or Q is 2,5-furan or b 2,4-thiophene, X is a bond, Y is sulphur, n is 1 and m is 2; with the proviso that $R_1R_2N$ is di $C_{1-3}$ alkylamino when Q is a furan or thiophene ring.

A further particularly preferred group of compounds are those of formula (II), in which either $R_1R_2N$ is dimethylamino, Q is a 2,5-furan, X is a bond, Y is sulphur, n is 1 and m is 2;

or $R_1R_2N$ is dimethylamino or pyrrolidino, piperidino, or hexamethylenimino, more preferably piperidino, Q is a 1,3-benzene, X is a bond, Y is oxygen, n is zero, and m is 3 or 4, more preferably 3;

and A represents N and B represents $CR_5$, or A represents $CR_5$ and B represents N, where $R_5$ is benzyl in which the methylene group is substituted by hydroxy;

with the proviso that, when Q is a furan ring, then preferably A is N and B is $CR_5$.

Particularly preferred compounds are 5-[[2-[[[5-[(dimethylamino)methyl]-2-furanyl]methyl]thio]ethyl]amino]-1-methyl-α-phenyl-1H-1,2,4-triazole-3-methanol, 1-methyl-α-phenyl-5-[[3-[3-(1-piperidinylmethyl)phenoxy]propyl]amino]-1H-1,2,4-triazole-3-methanol, 4-methyl-α-phenyl-5-[[3-[3-(1-piperidinylmethyl)phenoxy]propyl]amino]-4H-1,2,4-triazole-3-methanol, α-[1-methyl-5-[[3-[3-(1-piperidinylmethyl)phenoxy]propyl]amino]-1H-1,2,4-triazole-3-yl]-2-pyridinemethanol, 5-[[2-hydroxy-3-[3-(1-piperidinylmethyl)phenoxy]propyl]amino]-1-methyl-α-phenyl-1H-1,2,4-triazole-3-methanol, 5-[[3-[3-[(dimethylamino)methyl]phenoxy]propyl]amino]-1-methyl-α-phenyl-1H-1,2,4-triazole-3-methanol, 5-[[2-[[[5-[(dimethylamino)methyl]-3-thienyl]methyl]thio]ethyl]amino]-1-methyl-α-phenyl-1H-1,2,4-triazole-3-methanol, and their physiologically acceptable salts.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, citrates, tartrates, fumarates and benzoates. The compounds of formula (I) and their salts may also form hydrates, and the hydrates of the compounds of formula (I) are also to be considered at part of the invention. The compounds of formula (I) can exhibit tautomerism and the formulae are intended to cover all tautomers. Where optical isomers may exist the formulae are intended to cover all diastereoisomers and optical enantiomers. It should be understood that the present invention includes bioprecursors of the compounds of formula (I). The term bioprecursors means compounds which have a structure different to that of the compounds of formula (I) but which, upon administration to the animal or human being, are converted in the body into a compound of formula (I).

The compounds of formula (I) preferably in the form of a salt, may be formulated for administration in any convenient way and the invention includes within its scope pharmaceutical compositions containing at least one compound according to formula (I) adapted for use in human or veterinary medicine. Such compositions may be formulated in a conventional manner using one or more pharmaceutically acceptable carriers or excipients. Such compositions may also contain if required other active ingredients e.g. $H_1$-antagonists.

Thus the compounds of formula (I) may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of formula (I) may be formulated for parenteral administration by bolus injection or continuous infusion. Formulations for injection may be presented in unit dosage form in ampoules or in multidose containers, with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for reconstitution with a soluble vehicle e.g. sterile pyrogen-free water before use.

The compounds of formula (I) may also be formulated in rectal compositions such as suppositories or reetention enemas, e.g. containing conventional suppository bases such as cocoa butter or other glycerides.

For topical application, the compounds of formula (I) may be formulated as ointments, creams, gels, lotions, powders or sprays in a conventional manner.

For internal administration a convenient daily dosage regime of the compounds according to the invention would be 1 to 4 doses to the total of some 5 mg to 1 g per day, preferably 5 to 500 mg per day, dependent upon the condition of the patient.

It will be appreciated that in the methods for the preparation of compounds of formula (I) given below, for certain reaction steps it may be necessary to protect various reactive substituents in the starting materials for a particular reaction and subsequently to remove the protecting group. Such protection and subsequent deprotection may be particularly pertinent where $R_1$ and $R_2$ are hydrogen atoms and/or when $R_3$ is an alkyl group bearing a hydroxy substituent and/or when $R_5$ contains a hydroxy group. Standard protection and deprotection procedures can be employed, for example amines may be protected by formation of a phthalimide group which may subsequently be cleaved by treatment with a hydrazine, e.g. hydrazine hydrate or a primary amine, for example methylamine.

In describing the processes which may be used for preparing the compounds of formula (I) or intermediates useful in the preparation thereof, any of $R_1$ to $R_6$, A, B, Alk, Q, X, Y, Z, n, m, p, q, r, x and y in the various formulae are as defined in formula (I) unless otherwise stated.

Compounds of formula (I) may be prepared by cyclisation of an appropriate intermediate. Thus compounds of formula (I) in which $R_5$ is other than an aralkyl or heteroaralkyl group in which the alkyl portion is substituted by an acyloxy group or Y is other than $CHOR_6$ where $R_6$ is acyl can be prepared by cyclisation of a compound of formula (III)

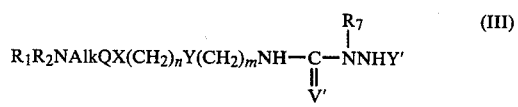

in which $R_7$ is a group as defined for $R_3$, V' is

and Y' is hydrogen where V is oxygen or sulphur and $R_5{}^c$ is a group as defined for $R_5$ or a group convertible thereto under the conditions of the cyclisation reaction; or V' is NH, $R_7$ is a group as defined for $R_3$ and Y' is

where Y" is sulphur, oxygen or NH; or V' is sulphur or oxygen, Y' is

and $R_7$ is a group as defined for $R_3$; or V' is $NR_3$, $R_7$ is hydrogen and Y' is

where Y" is as defined above.

Thus for example in one embodiment of the cyclisation process a compound of formula (I) in which A is N and B is the group $CR_5$ may be prepared by cyclisation of a compound of formula (IV)

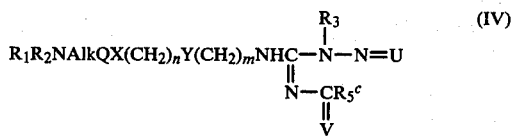

where V represents sulphur or more preferably oxygen and U represents two hydrogen atoms, in the absence or presence of a solvent, e.g. a hydrocarbon such as toluene, a ketone such as acetone, or water, and optionally with heating, for example, within the range 50° to 90°.

It may be convenient to prepare in situ compounds of formula (IV) in which U represents two hydrogen atoms by treating a compound of formula (IV) where U represents a divalent protecting group which can readily be removed to yield two hydrogen atoms, for example a benzylidene group, with an acid, e.g. hydrochloric acid, preferably with heating, and under such conditions cyclisation to give the corresponding compound of formula (I) will normally occur.

In a further embodiment of the cyclisation of compounds of formula (III), compounds of formula (I) may be prepared by cyclisation of a compound of formula (V)

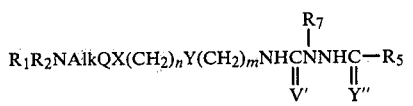
(V)

where $R_7$ is a group as defined for $R_3$, and either V' is NH and Y" is sulphur, oxygen or NH, or V' is sulphur or oxygen and Y" is NH; or $R_7$ is hydrogen, V' is $NR_3$ and Y" is sulphur.

When Y" represents sulphur then tautomerism with the adjacent NH group is possible (i.e.

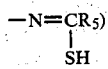

and the —SH group may be alkylated under standard conditions. The S-alkylated compound may also be used in the cyclisation process.

The cyclisation may be carried out by heating the compound (V) (e.g. within the range 80° to 150°) in the absence or presence of a solvent (e.g. acetonitrile or dimethylformamide), or under basic conditions (e.g. using aqueous potassium hydroxide).

In a convenient embodiment of this process an intermediate of formula (V) in which $R_7$ is a group as defined for $R_3$, V' is NH and Y" is oxygen; or $R_7$ is hydrogen, V' is $NR_3$ and Y" is oxygen may be prepared in situ by the reaction of an aminoguanidine (VI)

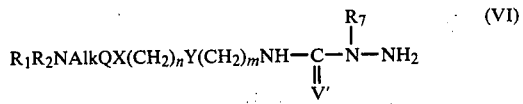
(VI)

with an acid $R_5COOH$ or with an activated derivative thereof. Suitable activated derivatives include acid halides, e.g. acid chlorides, alkylchloroformates, acid anhydrides including mixed anhydrides (e.g. acetic formic anhydride), esters such as alkyl esters, ortho esters (such as trialkylorthoesters, e.g. $R_5C(OEt_3)$ and (1-alkyl-2-pyridinyl) esters, or derivatives formed from a coupling agent such as carbonyldiimidazole or a carbodiimide such as dicyclohexylcarbodiimide.

The acid and the aminoguanidine (VI) may be heated together, under which conditions cyclisation of the intermediate (V) takes place directly to give a compound of formula (I). In the case of an activated derivative, an aprotic solvent. e.g. tetrahydrofuran may be used at temperatures from ambient to reflux. When using an acyl chloride as the activated derivative the reaction may also be carried out in the presence of a base, e.g. a tertiary amine such as pyridine, which may also be used as the solvent.

In general intermediates of formula (IV) may be prepared from the appropriate diamines by methods analogous to those described in British Patent Specification No. 2047238A, and intermediates of formula (V) may be prepared from the appropriate diamines by methods analogous to those described in British Patent Specification No. 20232133A and in European Patent Specification No. 48555. The aminoguanidines (VI) may be prepared as described in British Patent Specification No. 2023133A and European Patent Specification No. 48555.

Compounds of formula (I) in which Alk is $CH_2$ may be prepared by treating an aldehyde of formula (VII)

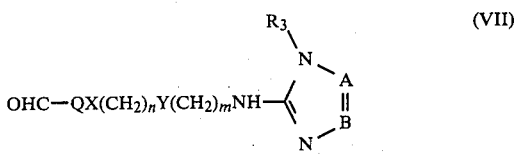
(VII)

with an amine $R_1R_2NH$, for example in a solvent such as tetrahydrofuran or an alkanol, e.g. ethanol, followed by reduction using for example a hydride reducing agent such as an alkali or alkaline earth metal borohydride, e.g. sodium borohydride or lithium aluminium hydride, or hydrogen and a metal catalyst such as palladium or platinum. The reactions may be carried out at a temperature of 0° to 80° C.

The intermediates of formula (VII) may be prepared from compounds of formula (VIII)

(VII)

in which W represents a protected aldehyde group, e.g. a cyclic acetal such as an ethylene acetal, by methods analogous to those described herein for preparing compounds of formula (I) from the appropriate diamine.

Compounds of formula (I) in which $R_5$ is an aralkyl or heteroaralkyl group in which the alkyl portion is substituted by hydroxy may be prepared by reacting the appropriate aldehyde or ketone with an organolithium compound ArLi or a Grignard reagent ArMgHal where Ar is an appropriate aryl, aralkyl, heteroaryl or heteroaralkyl group and Hal is halogen. The reaction may be carried out in a suitable solvent such as an ether e.g. diethyl ether, tetrahydrofuran or a mixture thereof at a temperature of from —70° to 50°, preferably —70° to to 20° for the reaction with ArLi and at 0° to 50° for the reaction with ArMgHal. The aldehyde or ketone starting material may be prepared as described in British Patent Specification No. 2075007A and European Patent Specification No. 48555.

Compounds of formula (I) in which $R_5$ has one meaning may be converted into compounds of formula (I) in which $R_5$ has another meaning using standard methods of interconversion.

Thus, compounds in which $R_5$ represents an aralkyl or heteroaralkyl group in which the alkyl portion is substituted by an acyloxy group, or Y represents $CHOR_6$ where $R_6$ is acyl, may be prepared by reacting the corresponding alcohol with an activated derivative (e.g. an acid chloride or an acid anhydride) of an appropriate acid. The reaction may be carried out at room temperature, optionally in the presence of a solvent (e.g. pyridine, tetrahydrofuran, acetone or dimethylformamide), and preferably in the presence of a base (e.g. pyridine, triethylamine or an alkali metal carbonate such as potassium carbonate).

Compounds in which $R_5$ represents an aralkyl or heteroaralkyl group in which the alkyl portion is substituted by an alkoxy group may be prepared from the corresponding alcohol by treatment with an halogenating agent, for example thionyl chloride, followed by reaction of the resulting halocompound with an appropriate alkanol in the presence of sodium at a temperature within the range 20°–50°. Alternatively the intermediate halocompound may be treated with an appropriate alkanol in a solvent such as dimethylformamide, in the presence of a strong base such as sodium hydride, at a temperature within the range 20°-100°.

Where the product of any of the above processes is a free base and an acid addition salt, in particular a physiologically acceptable salt is required, the salt may be formed in conventional manner. Thus, for example, a generally convenient method of forming the salts is to mix appropriate quantities of the free base and the acid in an appropriate solvent(s) e.g. an alcohol such as ethanol or an ester such as ethyl acetate. The invention also includes interconversion of one salt of the compound of formula (I) into another.

The invention is illustrated but not limited by the following Examples and Preparations, in which temperatures are in °C.

Unless otherwise stated the silica used for column chromatography was Merck Kieselgel 60(7734).

T.l.c. refers to thin layer chromatography and this and preparative chromatography were carried out on silica using, unless otherwise stated, one of the following solvent systems:

System A: Dichloromethane:ethanol:0.88 ammonia (50:8:1)

System B: Dichloromethane:ethanol:0.88 ammonia (100:8:1)

System C: Dichloromethane:ethanol:0.88 ammonia (75:8:1)

PREPARATION 1

Methyl N-[2-acetoxy-[2-(phenyl)-acetyl]]-1-methyl-2-(phenylmethylene)hydrazine carboximidothioate A solution of acetyl chloride (11.35 g) in dry ether (50 ml) was slowly added to a solution of mandelic acid (20 g) in ether (100 ml). The solution was heated at reflux for 3 days, before it was evaporated to leave a pale yellow oil. This oil was heated at reflux for 3 h with thionyl chloride (31 g). The thionyl chloride was removed by azeotropic distillation with toluene to leave an oil (27.7 g) which was used without further purification.

This oil was dissolved in toluene (50 ml) and added to a suspension of triethylamine (5.8 g) and methyl 1-methyl-2-(phenylmethylene)hydrazine carboximidothioate hydrochloride (6.9 g) in dry toluene (180 ml). The reaction was stirred at room temperature for 15 h, poured onto water and extracted with ether. The organic extract was dried (MgSO$_4$) and evaporated to give the title compound as a cream solid (6.3 g).

NMR (CDCl$_3$): 2.25, s, (1H); 2.3–2.8, m, (10H); 3.95, s, (1H); 6.7, s, (3H); 7.8, s, (3H); 7.9, s, (3H).

PREPARATION 2

(i) 2-[2-Hydroxy-3-[3-(1-piperidinylmethyl)phenoxy]propyl]-1H-isoindole-1,3-(2H)-dione A mixture of 2-(oxiranylmethyl)-1H-isoindole-1,3-(2H)-dione (9.10 g) and 3-(1-piperidinylmethyl)phenol (8.55 g) was heated at 130° C. under nitrogen for 10 minutes. The resulting mixture was dissolved in chloroform (100 ml), washed with 1N sodium hydroxide (2×25 ml), dried (MgSO$_4$) and evaporated to give the title compound as a gum (17.65 g).

T.l.c. system B; Rf 0.60.

(ii) 1-Amino-3-[3-(1-piperidinylmethyl)phenoxy]-2-propanol

A solution of 2-[2-hydroxy-3-[3-(1-piperidinylmethyl)phenoxy]propyl]-1H-isoindole-1,3-(2H) dione (17.6 g) and hydrazine hydrate (2.5 g) in ethanol (60 ml) was heated under reflux for 3 h. The resulting mixture was evaporated to a solid residue which was suspended in 1N hydrochloric acid (30 ml) and filtered. The filtrate was basified with an excess of potassium carbonate and extracted with isopropanol (3×40 ml). The isopropanol extracts were dried (Na$_2$CO$_3$) and evaporated to a gum which was chromatographed using System A. Crystallisation of the product from n-hexane:ether (20:1) gave the title compound as colourless grains (7.7 g), m.p. 74°–76.5°.

PREPARATION 3

5-[[3-(3-Formylphenoxy)propyl]amino]-1-methyl-α-phenyl-1H-1,2,4-triazole-3-methanol acetate (ester).

A solution of 3-[3-(1,3-dioxolan-2-yl)phenoxy]propanamine (6.0 g) and compound A*(11.33 g) in toluene (300 ml) was stirred at 20° for 4 h, 5N hydrochloric acid (30 ml) was added and the mixture was stirred at 20° for a further 18 h. The acidic layer was separated, washed with toluene basified with 2N sodium carbonate and extracted with ethyl acetate. The extract was dried and evaporated to give a gum (9.0 g) which was chromatographed on activated alumina [Phase Separations Ltd (UG1)] using ether:ethyl acetate:methanol 50:50:1 as eluent to give the title compound (1.4 g) as a foam. T.l.c. System B Rf 0.7.

* Compound A = methyl-N-[2-acetyloxy-[2-(phenyl)-acetyl]]-1-methyl-2-(phenylmethylene) hydrazine carboximidothioate

EXAMPLE 1(a)

5-[[2-Hydroxy-3-[3-(1-piperidinylmethyl)phenoxy]propyl]amino]-1-methyl-α-phenyl-1H-1,2,4-triazole-3-methanol A solution of 1-amino-3-[3-(1-poperidinylmethyl)phenoxy]-2-propanol (2.0 g) and methyl-N-[2-acetyloxy-[2-(phenyl)acetyl]]-1-methyl-2-(phenylmethylene) hydrazine carboximidothioate, compound A (3.19 g) in toluene (60 ml) was stirred at 20° for 4 h, 5N hydrochloric acid (9 ml) was added and the mixture was stirred at 20° for 16 h and heated on a steam bath for 15 min. The acidic layer was separated, washed with toluene, basified with saturated aqueous sodium bicarbonate, washed with toluene, and the aqueous layer basified with 5N sodium hydroxide. The basic layer was extracted with hot 4-methyl-2-pentanone (3×100 ml) and the extracts washed with brine, dried, and concentrated in vacuo to a volume of 150 ml whereupon crystallisation occurred. The resulting solid (1.2 g) was collected on a filter and recrystallised from 2-propanol to give the title compound (0.63 g) as a white solid m.p. 154°–157°.

Found: C, 66.2; H, 7.2; N, 15.2; C$_{25}$H$_{33}$N$_5$O$_3$ requires: C, 66.5; H, 7.4; N, 15.5%

EXAMPLE 1(b)

Similarly prepared from Compound A (1.5 g) and 3-[3-(dimethylaminomethyl)phenoxy]propanamine (0.74 g), except that the 4-methyl-2-pentanone extract was evaporated in vacuo and the residue (1.3 g) was chromatographed using System A as eluent, was 5-[[3-

[3-[(dimethylamino)methyl]phenoxy]propyl]amino]-1-methyl-α-phenyl-1H-1,2,4-triazole-3-methanol hydrate (0.31 g) as a white foam.

Found: C, 63.7; H, 7.3; N, 16.6. $C_{22}H_{29}N_5O_2.1H_2O$ requires: C, 63.9; H, 7.59; N, 16.9%

N.m.r. (CDCl$_3$–DMSO): 2.4–2.92, m, (6H); 3.05–3.33, m (3H); 4.4, s, (1H); 4.65, s(br), (1H); 5.58, s, (br), (1H); 5.98, t, (2H); 6.4–6.75, s+s+q, (7H); 7.85, s, (6H); 8.0, quintet, (2H).

EXAMPLE 1(c)

Similarly prepared from Compound A (1.5) and 2-[2-[3-(1-piperidinylmethyl)phenoxy]ethoxy]ethanamine (0.99 g), with exceptions that the aqueous phase was extracted with hot ethyl acetate (6×50 ml) at pH 7 and chromatographed using dichloromethane:ethanol:0.88 ammonia (80:8:1), was 1-methyl-α-phenyl-5-[[2-[2-[3-(1-piperidinylmethyl)phenoxy]ethoxy]ethyl]amino]-1H-1,2,4-triazole-3-methanol (0.45 g) as a clear gum.

Found: C, 66.95; H, 7.75; N, 14.65; $C_{26}H_{35}N_5O_3$ requires: C, 67.07; H, 7.58; N, 15.04%

N.m.r. (CDCl$_3$): 2.4–2.9, m, (6H); 3–3.35, m, (3H); 4.3, s, (1H); 5.6, t, (1H); 5.95, m, (2H); 6.27–6.8, m, (5H); 6.67, 2 xs, (6H); 7.75, m, (4H); 8.56, m, (6H).

EXAMPLE 1(d)

5-[[2-[[[5-[(Dimethylamino)methyl]-3-thienyl]methyl]thio]ethyl]amino]-1-methyl-α-phenyl-1H-1,2,4-triazole-3-methanol A solution of 4-[[[2-(aminoethyl)]thio]methyl]-N,N,-dimethyl-2-thiophene-methanamine (1.09 g) and compound A (2 g) in toluene (40 ml) was stirred at 20° for 4 h. 5N hydrochloric acid (5 ml) was added and the mixture was stirred at 20° for 16 h, then heated on the steam bath for 10 min. The acidic layer was basified to pH 3 with sodium bicarbonate, washed with toluene, basified to pH 9 with sodium carbonate and extracted with ethyl acetate. The ethyl acetate extract was dried, and evaporated to give a gum which was chromatographed using System B as eluent to give the title compound (0.45 g) as a fawn coloured foam. N.m.r. (CDCl$_3$+DMSO): 2.35–2.85, m, (5H); 3.01, s, (1H); 3.12, s, (1H); 4.33, s, (1H); 4.62, t, (1H); 5.75, br, (1H); 6.40, s, (2H); 6.45, s, (2H); 6.55, s, (3H); 6.5–6.7, t, (2H); 7.35, t, (2H); 7.75, s, (6H). T.l.c. System A Rf 0.5.

EXAMPLE 2

α-(2-Furanyl)-1-methyl-5-[[3-[3-(1-piperidinylmethyl)phenoxy]propyl]amino]-1H-1,2,4-triazole-3-methanol n-Butyllithium (1.55M in n-hexane, 5.96 ml) was added dropwise to a stirred solution of furan (0.16 ml) in anhydrous tetrahydrofuran (20 ml), under nitrogen at −40°. The stirred solution was allowed to warm slowly to 20°, heated under reflux for 3 h, added dropwise at 0° to a solution of 1-methyl-5-[[3-[3-(1-piperidinylmethyl)phenoxy]propyl]amino]-1H-1,2,4-triazole-3-carboxaldehyde (1.0 g) in tetrahydrofuran (10 ml), and the resulting solution was stirred at 20° for 18 h. Water (20 ml) was added, the mixture concentrated, extracted with ethyl acetate and the extract was dried and evaporated. The residual oil (0.9 g) was chromatographed using System C to give the title compound (0.16 g) as a brown oil.

N.m.r. (CDCl$_3$) 2.6, m, (1H); 2.76, t, (1H); 3.06–3.08, m, (2H); 3.23, m, (1H); 3.65, m, (2H); 4.25, s, (1H); 5.48, t, (1H); 5.86, t, (2H); 6.38, q, (2H); 6.45, s, (3H); 6.56, s, (2H); 7.62, m, (4H); 7.88, quintet, (2H); 8,36, m, (6H).

T.l.c. System A Rf 0.7.

EXAMPLE 3

1-Methyl-α-phenyl-5-[[3-[3-(1-piperidinylmethyl)phenoxy]propyl]amino]-1H-1,2,4-triazole-3-methanol compound with fumaric acid and ethyl acetate: 40:56:5

3-[3-(1-Piperidinylmethyl)phenoxy]propanamine (0.72 g) and methyl N-[2-acetyloxy-[2-(phenyl)acetyl]]-1-methyl-2-(phenylmethylene)hydrazine carboximidothioate (1.1 g) were heated together as a melt for 2 h at 60° to give a gum. This gum was dissolved in toluene and stirred for 15 h with 5N hydrochloric acid. The pH of the aqueous phase was adjusted to pH 7 with sodium carbonate and washed with toluene and ethyl acetate. The aqueous phase was basified to pH 10 with sodium carbonate and extracted with ethyl acetate. The organic extracts at pH 10 were dried (MgSO$_4$) and evaporated to leave an oil (1.1 g). This oil was chromatographed using dichloromethane:ethanol:0.88 ammonia (150:8:1) as eluent to give a white solid (0.25 g) m.p. 42°–52°. This solid (0.112 g) was dissolved in ethyl acetate and treated with a solution of fumaric acid (0.03 g) in ethyl acetate to precipitate the title compound which was collected as a white solid (0.095 g) m.p. 80°.

NMR (CDCl$_3$) of free base 2.4–2.9, m, (6H); 3.0–3.4, m, (3H); 4.31, s, (1H); 5.56, t, (1H); 5.93, t, (2H); 6.3–6.7, q+s+s, (7H); 7.5–7.75, m, (4H); 7.92, m, (2H); 8.3–8.7, m, (6H).

EXAMPLE 4

4-Methyl-α-phenyl-5-[[3-[3-(1-piperidinylmethyl)phenoxy]propyl]amino]-4H-1,2,4-triazole-3-methanol A mixture of DL mandelic acid (30.4 g) and N-amino-N$^1$-methyl-N$^{11}$-[3-[3-(1-piperidinylmethyl)phenoxy]propyl]guanidine hydroiodide (22.35 g) was heated from 40° to 125° and maintained at 125° as a melt for 6 h.

The hot melt was extracted with hot water (250 ml) and the aqueous extract was basified to pH 8 with solid sodium carbonate, and extracted into ether. The ether extract was cooled at 5° to give a white solid which was washed with boiling ethyl acetate to leave the title compound as a white solid (0.18 g) m.p. 186–8°.

Assay Found: C, 68.9; H, 7.7; N, 16.0; $C_{25}H_{33}N_5O_2$ requires: C, 68.9; H, 7.6; N, 16.1%

EXAMPLE 5

[4-Methyl-α-phenyl-5-[[3-[3-(1-piperidinylmethyl)phenoxy]propyl]amino]-4H-1,2,4-triazole-3-methanol]acetate (ester) hydrate A solution of 4-methyl-α-phenyl-5-[[3-[3-(1-piperidinylmethyl)phenoxy]propyl]amino]-4H-1,2,4-triazole-3-methanol (0.10 g) and acetic acid anhydride (0.03 ml) in pyridine (2 ml) was stirred at room temperature for 16 h. Saturated sodium carbonate solution was added and the suspension was extracted with ethyl acetate. The organic phase was washed with water and brine, and evaporated under reduced pressure. The residue was crystallised from isopropyl acetate to give the title compound as a white solid (0.074 g), m.p. 89°–91° C.

Assay Found: C, 64.9; H, 7.5; N, 13.8; $C_{27}H_{35}N_5O_3H_2O$ requires: C, 65.3; H, 7.4; N, 14.1%

EXAMPLE 6

α-[1-Methyl-5-[[3-[3-(1-piperidinylmethyl)phenoxy]propyl]amino]-1H-1,2,4-triazol-3-yl]-2-pyridinemethanol n-Butyllithium (1.6M in n-hexane, 8.12 ml) was added dropwise during 15 min to a stirred solution of 2-bromopyridine (1.86 g, 1.12 ml) in anhydrous ether (10 ml) at −70°, under nitrogen. The brown solution was stirred at −70° for 0.5 h before a solution of 1-methyl-5-[[3-[3-(1-piperidinylmethyl)phenoxy]propyl]amino]-1H-1,2,4-triazole-3-carboxaldehyde (2.0 g) in anhydrous tetrahydrofuran (20 ml) was added dropwise at −70° and the solution was stirred at −40° for 2 h before water (20 ml) was added and the mixture was allowed to stand overnight at 20°. The mixture was concentrated extracted with ethyl acetate and the extract was dried and evaporated to give an oil (2.5 g) which was chromatographed using System C as eluent to give a solid (0.48 g). This was crystallised from ethyl acetate to give the title compound (0.25 g) as a white powder m.p. 152°–154° (d).

Found: C, 65.9; H, 7.4; N, 19.1; $C_{24}H_{32}N_6O_2$ requires: C, 66.0; H, 7.4; N, 19.2%

EXAMPLE 7

5-[[2-[[[5-[(Dimethylamino)methyl]-2-furanyl]methyl]thio]ethyl]amino]-1-methyl-α-phenyl-1H-1,2,4-triazole-3-methanol dihydrochloride A solution of 2-[[[5-[(dimethylamino)methyl]-2-furanyl]methyl]thio]ethanamine (3.09 g) and methyl-N-[2-acetyloxy-[2-(phenyl)acetyl-]]-1-methyl-2-(phenylmethylene)hydrazine-carboximidothioate (5.9 g) in toluene (110 ml) was stirred at room temperature for 3 h. A further quantity of methyl-N-[2-acetyloxy-[2-(phenyl)acetyl]]-1-methyl-2-(phenylmethylene)hydrazine-carboximidothioate (0.3 g) was added and the mixture stirred at room temperature for 1.5 h. 2M hydrochloric acid (22.5 ml) was then added to the reaction mixture and the mixture heated on a steam bath for 1 h. The aqueous layer was adjusted to pH 6 with potassium carbonate and washed with toluene (2×30 ml). The acidic aqueous layer was basified with potassium carbonate and extracted with diethyl ether and ethyl acetate. The combined organic extracts were dried and evaporated to give a brown gum, which was chromatographed on silica using dichloromethane:ethanol:ammonia (65:8:1) to give a brown gum (1.35 g). This was dissolved in methyl acetate and treated with ethereal hydrogen chloride to give a white solid which was triturated with dry ether to give the title compound (1.3 g) as a fine white solid, mp 55°–60° softens.

Nmr (CD$_3$OD): 2.5, m, (5H); 3.3, d, (1H); 3.6, d, (1H); 4.15, s, (1H); 5.6, s, (2H); 6.3, m, (7H); 7.15, m, (8H).

EXAMPLE 8

5-[[3-[3-[[(2-Furanylmethyl)amino]methyl]phenoxy]propyl]amino]-1-methyl-α-phenyl-1H-1,2,4-triazole-3-methanol A solution of 5-[[3-(3-formylphenoxy)propyl]amino]-1-methyl-α-phenyl-1H-1,2,4-triazole-3-methanol acetate (ester) (1.0 g) and furfurylamine (5 ml) in ethanol (30 ml) was stirred at 21° for 1.5 h before a suspension of sodium borohydride (1.3 g) in ethanol (10 ml) was added and stirring was continued for a further 16 h at 21°. Water (20 ml) was added, the mixture concentrated to remove ethanol and the aqueous residue extracted with 4-methylpentan-2-one. The extract was dried and evaporated to give an oil. Excess furfurylamine was removed in vacuo and the residue was dissolved in 2N hydrochloric acid, the acidic layer washed with ethyl acetate, basified (pH 9) with sodium carbonate, and extracted with 4-methylpentan-2-one. The extract was washed with water, dried and evaporated to give a brown gum (0.65 g) which was chromatographed on silica (Merck No. 7729) using System B as eluent to give the title compound (0.5 g) as a pale orange gum.

T.l.c. System B Rf 0.35.

N.m.r. (CDCl$_3$) 2.50, db, (2H); 2.6–2.84, m, (5H; 3.14–3.4, m, (2H); 3.24, d, (1H); 3.70, dd, (1H); 3.82, dd, (1H); 4.28, s, (1H); 5.5, t, (1H) 5.92, t, (2H); 6.23, s, (2H); 6.25, s, (2H); 6.44, q(dt) (2H); 6.56, s, (3H); 6.6–8, m, (2H); 7.94, m, (2H).

EXAMPLE 9

5-(Methoxyphenylmethyl)-4-methyl-N-[3-[3-(1-piperidinylmethyl)phenoxy]propyl]-4H-1,2,4-triazole-3-amine compound with tartaric acid (1:1)

A solution of 4-methyl-α-phenyl-5-[[3-[3-(1-piperidinylmethyl)phenoxy]propyl]amino]-4H-1,2,4-triazole-3-methanol (0.37 g) in thionyl chloride (3.0 ml) was stirred at room temperature for 0.5h. The solvent was removed in vacuo. The residual pink foam was dissolved in dry methanol (10 ml) and added dropwise to a solution of sodium (0.17 g) in dry methanol (10 ml). The reaction solution was stirred at room temperature for 0.5h, poured onto water, and extracted with ethyl acetate. The organic extract was dried and evaporated to give a gum (0.3 g). This gum was dissolved in ethyl acetate and treated with an excess of tartaric acid in ethyl acetate to give the title compound as a white solid (0.26 g) m.p.=88° softens.

N.m.r. (CD$_3$OD) 2.5–3.1, m, (9H); 4.5, s, (1H); 5.6, s, (2H); 5.8, s, (2H); 5.9, t, (2H); 6.48, t, (2H); 6.60, s, (3H); 6.80, s, (3H); 6.85, m, (4H); 7.85, m, (2H); 8.2, m, (6H).

EXAMPLE 10

5-[[2-[[[5-[(Dimethylamino)methyl]-2-furanyl]methyl]thio]ethyl]amino]-1-methyl-α-phenyl-1H-1,2,4-triazole-3-methanol A solution of 2-[[5-[(dimethylamino)methyl]-2-furanylmethyl]thio]ethanamine (3.09 g) and methyl-N-[2-acetyloxy-[2-(phenyl)acetyl[[-1-methyl-2-(phenylmethylene)hydrazinecarboximidothioate (compound A) (5.9 g) in toluene (110 ml) was stirred at room temperature for 3h and a further quantity of compound A (0.3 g) was added. The mixture was stirred at room temperature for a further 1.5h, 2M hydrochloric acid (22.5 ml) was added, and the mixture was heated on a steam bath for 1h. The aqueous layer was adjusted to pH 6 with potassium carbonate and washed with toluene. The acidic aqueous layer was then basified with potassium carbonate and extracted with diethyl ether and ethyl acetate. The combined organic extracts were dried and evaporated to leave a brown gum which was chromatographed using dichloromethane:ethanol:ammonia (65:8:1) to give a brown gum (1.95 g). A portion of this gum (0.5 g) was dissolved in dry tetrahydrofuran and filtered through "Florisil" (an activated magnesium silicate). The filtrate was concentrated to a small volume to give the title compound (0.32 g) as a white solid, m.p. 121°–122.5°.

Found: C, 60.0; H, 6.9; N, 17.3; $C_{20}H_{27}N_5O_2S$ requires: C, 59.8; H, 6.8; N, 17.4%

EXAMPLES OF PHARMACEUTICAL COMPOSITIONS

| Tablets | mg/tablet |
|---|---|
| Active ingredient | 5.0 to 125.0 |
| Microcrystalline Cellulose USP | 293.5 to 173.5 |
| Magnesium Stearate BP | 1.5 |
| Compression weight | 300.0 |

The drug is sieved through a 250 μm sieve, blended with the excipients and compressed using 9 mm diameter punches. Other strengths may be prepared by altering the compression weight and using punches to suit.

The tablets may be film coated using suitable film forming polymers such as hydroxypropyl methyl cellulose using standard techniques. Alternatively the tablets may be sugar coated.

| Capsules | mg/capsule |
|---|---|
| Active ingredient | 5.0 to 125.0 |
| Starch 1500* (USP) | 243.5 to 123.5 |
| Magnesium Stearate BP | 1.5 |
| Fill weight | 250.0 |

*A form of directly compressible starch

The active ingredient is sieved through a 250 μm sieve and blended with the excipients. The mix is filled into No. 2 hard gelatin capsules using suitable machinery. Other doses may be prepared by altering the fill weight, and, if necessary, changing the capsule size.

| Injection for Intravenous Administration | % w/v |
|---|---|
| Active ingredient | 0.20 to 0.50 |
| Water for Injection B.P to | 100.0 |

Sodium chloride may be added to adjust the tonicity of the solution and the pH may be adjusted to that of maximum stability using either dilute acid or alkali. The solution is prepared, clarified and filled under nitrogen, or other inert gas, into appropriate sized ampoules sealed by the fusion of glass. The injection is sterilised by heating in an autoclave using one of the acceptable cycles. Alternatively the solution may be sterilised by filtration and filled into sterile ampoules under aseptic conditions.

| Syrup | mg/5 ml dose |
|---|---|
| Active ingredient | 5.0 to 250.0 |
| Sucrose | 2795.0 to 2550.0 |
| Glycerine | 500.0 |
| Buffer | |
| Flavour | as necessary |
| Colour | |
| Distilled water to | 5.0 ml |

The active ingredient, buffer, flavour, preservative and colour are dissolved in some of the water. The remainder of the water is heated to approximately 80° C. and the sucrose is dissolved in this water and cooled. The two solutions are mixed, adjusted to volume and clarified by filtration. Alternatively, the active ingredient, sucrose, buffer, flavour, colour and preservative may be mixed and the powder filled into bottles for later reconstitution by the addition of water.

In the above examples the active ingredient is preferably 5-[[2-[[[5-[(dimethylamino)methyl]-2-furanyl]methyl]thio]amino]-1-methyl-α-phenyl-1H-1,2,4-triazole-3-methanol in the form of a physiologically acceptable salt, for example the hydrochloride.

I claim:

1. A compound of formula (I)

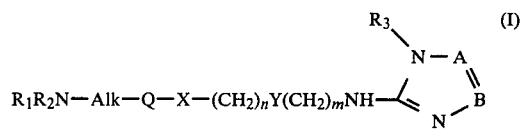

or a physiologically acceptable salt or hydrate thereof, in which $R_1$ represents hydrogen, $C_{1-14}$ alkyl, $C_{3-8}$ cycloalkyl, $C_{3-6}$ alkenyl, ar $C_{1-6}$ alkyl wherein ar is phenyl or phenyl substituted with one or more $C_{1-3}$ alkyl or $C_{1-3}$ alkoxy groups or halogen atoms; heteroaralkyl wherein the heteroaryl portion is a thienyl, pyridinyl or furyl, the heteroaryl ring may be unsubstituted or substituted by $C_{1-3}$ alkyl, $C_{1-3}$ alkoxy, hydroxy, hydroxy $C_{1-6}$ alkyl, amino $C_{1-6}$ alkyl, $C_{1-6}$ alkylamino $C_{1-6}$ alkyl, di-$C_{1-6}$ alkylamino $C_{1-6}$ alkyl or halogen, and the alkyl portion of the heteroalkyl group is a straight or branched $C_{1-4}$ alkyl chain and the heteroaryl portion is linked to the alkyl portion through a carbon atom; trifluoro $C_{1-6}$ alkyl or $C_{1-6}$ alkyl substituted by hydroxy, $C_{1-6}$ alkoxy, amino, $C_{1-6}$ alkylamino, di-$C_{1-6}$ alkylamino or $C_{3-8}$ cycloalkyl; and $R_2$ represents hydrogen or $C_{1-4}$ alkyl; or $R_1$ and $R_2$ may together with the nitrogen atom to which they are attached form piperidino, pyrrolidino, morpholino, 4-methylpiperidino, hexamethyleneimino tetrahydropyridino;

Alk represents a straight or branched alkylene chain of 1 to 3 carbon atoms,

Q represents a furan or thiophene ring in which incorporation into the rest of the molecule is through bonds at the 2- and 5-positions, the furan or thiophene ring optionally bearing a further substituent $R_4$ adjacent to the group $R_1R_2$N-Alk-; or Q represents a thiophene ring in which incorporation into the rest of the molecule is through bonds at the 2- and 4-positions, the thiophene ring optionally bearing a further substituent $R_4$ adjacent to the group $R_1R_2$NAlk with the proviso that when the group $R_1R_2$NAlk is in the 4-position then the group $R_4$ is in the 5-position; or Q represents a benzene ring in which incorporation into the rest of the molecule is through bonds at the 1- and 3- or 1- and 4-positions;

$R_4$ represents halogen or $C_{1-4}$ alkyl which may be substituted by hydroxy or $C_{1-4}$ alkoxy;

X represents oxygen, sulphur, —NH—, methylene or a bond;

Y represents oxygen, sulphur, methylene or a bond;

n represents zero, 1, 2 or 3, and m is an integer from 2 to 5, with the provisos that (a) the total number of atoms in te chain $X(CH_2)_nY(CH_2)_m$ is an integer from 3 to 8, (b) when X and Y represent oxygen or sulphur then n is 2 or 3, (c) when X represents —NH— then Q is a benzene ring and Y represents methylene or a bond, and (d) when Q represents a benzene ring, X represents oxygen, and n represents 1, then m may additionally represent 1 and Y may additionally represent —CHOR$_6$ where $R_6$ represents hydrogen, aroyl, or ar $C_{2-7}$ alkanoyl, wherein ar is as defined above, or $C_{1-6}$ alkanoyl; and R₃ represents hydrogen, $C_{1-6}$ alkyl, $C_{3-6}$ alkenyl, ar $C_{1-6}$ alkyl, wherein ar is as defined above, or $C_{2-6}$ alkyl substituted by hydroxy or $C_{1-6}$ alkoxy;

either A represents N and B represents CR₅; or A represents CR₅ and B represents N; and R₅ represents an ar $C_{1-6}$ alkyl, wherein ar is as defined above or heteroar $C_{1-6}$ alkyl group, wherein the heteroaryl portion is thienyl, pyridinal or furyl, and optionally substituted by a $C_{1-3}$ alkyl group, with the alkyl portion of the group linked to the heteroaryl portion through a carbon atom, and in which the alkyl group of the ar $C_{1-6}$ alkyl and heteroar $C_{1-6}$ alkyl groups is substituted by hydroxy, $C_{1-6}$ alkoxy, aroyloxy or ar $C_{2-7}$ alkanoyloxy wherein ar is as defined above, or $C_{1-6}$ alkanoyloxy.

2. A compound as claimed in claim 1 in which:

R₁ represents $C_{1-8}$ alkyl, $C_{1-4}$ alklyl substituted by a trifluoromethyl group, $C_{2-4}$ alkyl substituted by hydroxy or a di $C_{1-3}$ alkyl amino group, $C_{5-7}$ cycloalkyl, $C_{3-5}$ alkenyl, phenyl $C_{1-3}$ alkyl or a thienyl, pyridinal of furyl, optionally substituted by a $C_{1-3}$ alkyl group;

R₂ represents hydrogen or methyl; or

R₁R₂N represents piperidino, morpholino, 4-methylpiperidino, pyrrolidino, hexamethyleneimino or tetrahydropyridino;

Alk represents methylene;

Q represents a benzene ring incorporated into the rest of the molecule through bonds at the 1- and 3-positions; or a furan ring incorporated into the rest of the molecule through bonds at the 2- and 5- positions optionally bearing a substituent R₄ adjacent to the group R₁R₂NAlk where R₄ is $C_{1-4}$ alkyl; or a thiophene ring incorporated into the rest of the molecule through bonds at the 2- and 4-positions with the substituent R₁R₂NAlk in the 2-position; with the provisos that when Q is a benzene ring as just defined, then X is a bond, n is zero, Y is oxygen and m is 3, 4 or 5, or X and Y both represent oxygen and n and m are both 2, or X is oxygen, Y is CHOH and n and m are both 1; and when Q is a furan or thiophene ring as just defined, then X is a bond and either Y is sulphur or CH₂, n is 1 and m is 2, or Y is oxygen, n is 1 and m is 3;

R₃ represents hydrogen or $C_{1-6}$ alkyl

R₅ represents phenyl $C_{1-3}$ alkyl or heteroaryl $C_{1-3}$ alkyl in which the alkyl portion is substituted by hydroxy, $C_{1-4}$ alkanoyloxy or $C_{1-2}$ alkoxy and wherein the heteroaryl portion is thienyl, pyridyl or furyl.

3. A compound as claimed in claim 1 in which

R₁ represents $C_{1-8}$ alkyl, $C_{1-4}$ alkyl substituted by a trifluoromethyl group, $C_{2-4}$ alkyl substituted by hydroxy or a di $C_{1-3}$ alkyl amino group, $C_{5-7}$ cycloalkyl, $C_{3-5}$ alkenyl, phenyl $C_{1-3}$ alkyl, or a thienyl, pyridinyl or furyl optionally substituted by a $C_{1-3}$ alkyl group, R₂ represents hydrogen or methyl; or R₁R₂N represents piperidino, morpholino, 4-methylpiperidino, pyrrolidino, hexamethyleneimino or tetrahydropyridino;

Alk represents methylene;

Q represents a benzene ring incorporated into the rest of the molecule through bonds at the 1- and 3-positions; or a furan ring incorporated into the rest of the molecule through bonds at the 2- and 5-positions optionally bearing a substituent R₄ adjacent to the group R₁R₂NAlk where R₄ is $C_{1-4}$ alkyl; or a thiophene ring incorporated into the rest of the molecule through bonds at the 2- and 4-positions with the substituent R₁R₂NAlk in the 2-position; with the provisos that when Q is a benzene ring as just defined then X is a bond, n is zero, Y is oxygen and m is 3, 4 or 5, or X and Y represent oxygen and n and m are both 2, or X is oxygen, Y is CHOH and n and m are both 1; and when Q is a furan or thiophene ring as just defined then X is a bond and either Y is sulphur or CH₂, n is 1 and m is 2, or Y is oxygen, n is 1 and m is 3;

R₃ represents hydrogen or $C_{1-6}$ alkyl;

R₅ represents phenyl $C_{1-3}$ alkyl in which the alkyl portion is substituted by $C_{1-4}$ alkanoyloxy or $C_{1-2}$ alkoxy, or heteroaryl $C_{1-3}$ alkyl in which the alkyl portion is substituted by hydroxy, $C_{1-4}$ alkanoyloxy or $C_{1-2}$ alkoxy, and wherein the heteroaryl portion is thienyl, pyridyl or furyl.

4. A compound of formula (II)

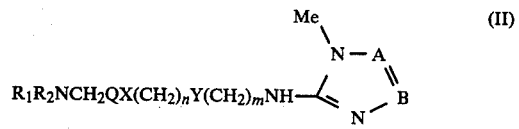

or a physiologically acceptable salt or hydrate thereof in which

R₁R₂N represents di $C_{1-3}$ alkylamino, furylmethylamino, or pyrrolidino, piperidino, 4-methylpiperidino, tetrahydropyridino or hexamethylenimino;

A represents N and B represents CR₅, or A represents CR₅ and B represents N, where R₅ represents phenyl $C_{1-3}$ alkyl or heteroaryl $C_{1-3}$ alkyl in which the alkyl portion is substituted by hydroxy and the heteroaryl portion is thienyl pyridyl or furyl; or phenyl $C_{1-3}$ alkyl in which the alkyl portion is substituted by $C_{1-4}$ alkanoyloxy or $C_{1-2}$ alkoxy;

either Q is 1,3-benzene and X is a bond, n is zero, Y is oxygen and m is 3 or 4; or X is oxygen, n is 1, Y is —CHOH— and m is 1; or Q is 2,5-furan or 2,4-thiophene, X is a bond, Y is sulphur, n is 1 and m is 2; with the proviso that R₁R₂N is di $C_{1-3}$ alkylamino when Q is a furan or thiophene ring.

5. A compound of formula (II)

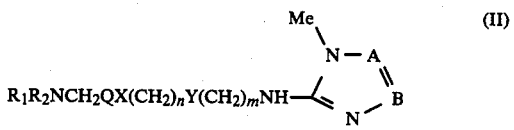

or a physiologically acceptable salt or hydrate thereof in which either R₁R₂N is dimethylamino, Q is 2,5-furan, X is a bond, Y is sulphur, n is 1 and m is 2;

or R₁R₂N is dimethylamino or pyrrolidino, piperidino, or hexamethylenimino, Q is 1,3-benzene, X is a bond, Y is oxygen, n is zero, and m is 3 or 4;

and A represents N and B represents CR₅, or A represents CR₅ and B represents N, where R₅ is benzyl in which the methylene group is substituted by hydroxy.

6. 5-[[2-[[[5-[(Dimethylamino) methyl]-2-furanyl]methyl]thio]ethyl]amino]-1-methyl-α-phenyl-1H-1,2,4-triazole-3-methanol and physiologically acceptable salts thereof.

7. A compound as claimed in claim 1 which is selected from:

1-methyl-α-phenyl-5-[[3-[3-(1-piperidinylmethyl) phenoxy]propyl]amino]-1H-1,2,4-triazole-3-methanol 4-methyl-α-phenyl-5-[[3-[3-(1-piperidinylmethyl) phenoxy]propyl]amino]-4H-1,2,4-triazole-3-methanol and physiologically acceptable salts thereof.

8. A compound as claimed in claim 1 which is selected from:

α-[1-methyl-5-[[3-[3-(1-piperidinylmethyl)phenoxy]propyl]amino]-1H-1,2,4-triazol-3-yl]-2-pyridinemethanol 5-[[2-hydroxy-3-[3-(1-piperidinylmethyl)phenoxy]propyl]amino]-1-methyl-α-phenyl-1H, 1,2,4-triazole-3-methanol 5-[[3-[3-[(dimethylamino)methyl]phenoxy]propyl]amino]-1-methyl-α-phenyl-1H-1,2,4-triazole-3-methanol 5-[[2-[[[5-[(dimethylamino)methyl]-3-thienyl]methyl]thio]ethyl]amino]-1-methyl-α-phenyl-1H-1,2,4-triazole-3-methanol and physiologically acceptable salts thereof.

9. A pharmaceutical composition for the treatment of conditions mediated through $H_2$-receptors comprising an effective amount of a compound of formula (I) as defined in claim 1 together with at least one pharmaceutically acceptable carrier or diluent.

10. A method of treating a condition mediated through $H_2$-receptors which comprises administering to a patient an effective amount of a compound according to claim 1 to relieve said condition.

* * * * *